United States Patent
Ibrahim et al.

(10) Patent No.: US 7,762,131 B2
(45) Date of Patent: **\*Jul. 27, 2010**

(54) SYSTEM FOR PREDICTING CHANGES IN A DRILLING EVENT DURING WELLBORE DRILLING PRIOR TO THE OCCURRENCE OF THE EVENT

(76) Inventors: Emad B. Ibrahim, 320 Jackson Hill, Apt. #330, Houston, TX (US) 77007; Louis W. Elrod, 17010 Scenic Lakes Way, Houston, TX (US) 77095; Christopher M. Jones, 5235 Cypress Spring Dr., Missouri City, TX (US) 77459; Sara Shayegi, 12800 Briar Forest, 156, Houston, TX (US) 77077; Timothy O. Wiemers, 12730 Melvern Ct., Houston, TX (US) 77041; Roger L. Schultz, 4792 Red Oak Cir., Aubrey, TX (US) 76227; Craig Godfrey, 7560 Stonecrest, Dallas, TX (US) 75240

( * ) Notice: Subject to any disclaimer, the term of this patent is extended or adjusted under 35 U.S.C. 154(b) by 0 days.

This patent is subject to a terminal disclaimer.

(21) Appl. No.: 11/960,621

(22) Filed: Dec. 19, 2007

(65) Prior Publication Data

US 2008/0097735 A1    Apr. 24, 2008

Related U.S. Application Data

(62) Division of application No. 10/844,725, filed on May 12, 2004, now Pat. No. 7,337,660.

(51) Int. Cl.
*E21B 47/08* (2006.01)
(52) U.S. Cl. .................................. 73/152.55
(58) Field of Classification Search ............. 73/152.55; 166/252.1; 175/50
See application file for complete search history.

(56) References Cited

U.S. PATENT DOCUMENTS 3,159,214 A    12/1964    Carter ................ 166/252.1

(Continued)

FOREIGN PATENT DOCUMENTS

EP    0 386 810    9/1990

(Continued)

OTHER PUBLICATIONS van Riet, E.J., et al., "*Development and Testing of a Fully Automated System to Accurately Control Downhole Pressure During Drilling Operations*," Society of Petroleum Engineers, Inc., SPE 85310, presented at the SPE/IADC Middle East Drilling Technology Conference & Exhibition, Abu Dhabi, UAE, Oct. 20, 2003, pp. 1-12.

(Continued)

*Primary Examiner*—Hezron Williams
*Assistant Examiner*—Tamiko D Bellamy
(74) *Attorney, Agent, or Firm*—Fish & Richardson P.C.

(57) ABSTRACT

A system for drilling a wellbore includes a prediction unit operable to predict a change in a drilling event while the wellbore is being drilled and prior to the drilling event change occurring. The prediction unit monitors surface and downhole data and well inflows to predict drilling events. The prediction unit may activate alarms for predefined drilling conditions, such as a kick alarm to provide an early warning of a dangerous influx of formation fluids into the wellbore.

33 Claims, 3 Drawing Sheets

U.S. PATENT DOCUMENTS

| | | | |
|---|---|---|---|
| 3,871,218 A | 3/1975 | Louis | 73/152.41 |
| 4,225,314 A | 9/1980 | Macourt | 436/26 |
| 4,477,573 A | 10/1984 | Taufen | 436/33 |
| 4,492,862 A | 1/1985 | Grynberg et al. | 250/255 |
| 4,536,199 A | 8/1985 | Toon | 95/1 |
| 4,577,492 A | 3/1986 | Holba et al. | 73/61.5 |
| 4,676,313 A | 6/1987 | Rinaldi | 166/252.1 |
| 4,709,900 A | 12/1987 | Dyhr | 251/5 |
| 4,833,915 A | 5/1989 | Radd et al. | 73/152.04 |
| 4,845,981 A | 7/1989 | Pearson | 73/152.31 |
| 4,924,950 A * | 5/1990 | Niitsuma et al. | 175/50 |
| 5,077,471 A | 12/1991 | Smith, Jr. et al. | 250/260 |
| 5,220,504 A | 6/1993 | Holzhausen et al. | 702/12 |
| 5,249,461 A | 10/1993 | Ponder et al. | 73/152.18 |
| 5,317,111 A | 5/1994 | Orban et al. | 181/105 |
| 5,337,821 A | 8/1994 | Peterson | 166/250.07 |
| 5,388,456 A | 2/1995 | Kettel | 73/152.02 |
| 5,406,078 A | 4/1995 | Jacobson | 250/261 |
| 5,434,408 A | 7/1995 | Smith, Jr. et al. | 250/269.8 |
| 5,551,287 A | 9/1996 | Maute et al. | 73/152.02 |
| 5,857,522 A | 1/1999 | Bradfield et al. | 166/267 |
| 5,871,047 A | 2/1999 | Spath et al. | 166/250.01 |
| 5,871,053 A | 2/1999 | Stern | 166/401 |
| 5,992,519 A | 11/1999 | Ramakrishnan et al. | 166/250.15 |
| 6,035,952 A | 3/2000 | Bradfield et al. | 175/66 |
| 6,051,973 A | 4/2000 | Prammer | 324/303 |
| 6,057,784 A | 5/2000 | Schaaf et al. | 340/854.4 |
| 6,167,348 A | 12/2000 | Cannon | 702/13 |
| 6,176,323 B1 | 1/2001 | Weirich et al. | 175/40 |
| 6,176,326 B1 | 1/2001 | David et al. | 175/58 |
| 6,178,815 B1 | 1/2001 | Felling et al. | 73/152.19 |
| 6,179,066 B1 | 1/2001 | Nasr et al. | 175/45 |
| 6,234,258 B1 | 5/2001 | Karigan | 175/66 |
| 6,266,619 B1 | 7/2001 | Thomas et al. | 702/13 |
| 6,585,044 B2 | 7/2003 | Rester et al. | 166/250.1 |
| 6,661,000 B2 | 12/2003 | Smith et al. | 250/282 |
| 6,732,052 B2 | 5/2004 | Macdonald et al. | 702/6 |
| 6,888,127 B2 | 5/2005 | Jones et al. | 250/269.1 |
| 7,003,439 B2 * | 2/2006 | Aldred et al. | 703/10 |
| 7,337,660 B2 | 3/2008 | Ibrahim et al. | 73/152.55 |
| 7,367,411 B2 * | 5/2008 | Leuchtenberg | 175/48 |
| 7,571,644 B2 | 8/2009 | Ibrahim et al. | 73/152.55 |
| 2002/0016679 A1 | 2/2002 | Thomas et al. | 702/14 |
| 2002/0099505 A1 | 7/2002 | Thomas et al. | 702/12 |
| 2002/0112888 A1 | 8/2002 | Leuchtenberg | 175/48 |
| 2002/0120429 A1 | 8/2002 | Ortoleva | 703/2 |
| 2003/0079912 A1 | 5/2003 | Leuchtenberg | 175/48 |
| 2003/0220742 A1 | 11/2003 | Niedermayr et al. | 702/9 |
| 2004/0014196 A1 | 1/2004 | Coates et al. | 435/252.1 |
| 2004/0019427 A1 | 1/2004 | San Martin et al. | 702/6 |
| 2004/0040746 A1 | 3/2004 | Neidermayr et al. | 175/38 |
| 2004/0111216 A1 | 6/2004 | Kneissl et al. | 702/12 |
| 2004/0119471 A1 | 6/2004 | Blanz et al. | 324/303 |
| 2004/0268338 A1 * | 12/2004 | Gurpinar et al. | 717/169 |
| 2005/0038603 A1 | 2/2005 | Thomas et al. | 702/6 |
| 2005/0096847 A1 * | 5/2005 | Huang | 702/9 |
| 2005/0274513 A1 | 12/2005 | Schultz et al. | 166/254.2 |
| 2007/0168056 A1 | 7/2007 | Shayegi et al. | 700/48 |
| 2007/0289740 A1 | 12/2007 | Thigpen et al. | 166/250.01 |

FOREIGN PATENT DOCUMENTS

| | | |
|---|---|---|
| EP | 0 436 242 B | 4/1994 |
| GB | 2 365 039 B1 | 10/2002 |
| WO | WO 99/00575 | 1/1999 |
| WO | WO 00/04269 | 1/2000 |
| WO | PCT/GB01/03216 | 7/2000 |
| WO | WO 00/79092 | 12/2000 |
| WO | WO 02/06634 | 1/2002 |
| WO | WO 03/071091 | 8/2003 |

OTHER PUBLICATIONS

Kardolus, et al., "*Formation Testing While Underbalanced Drilling*," Society of Petroleum Engineers, Inc., SPE 38754, presented at 1997 SPE Annual Technical Conference and Exhibition, San Antonio, TX, Oct. 5, 1997, pp. 1-8.

Larsen, Leif, et al., "*Inflow Predictions and Testing While Underbalanced Drilling*," Society of Petroleum Engineers, Inc., SPE 56684, presented at SPE Annual Technical Conference & Exhibition, Houston, TX Oct. 3, 1999, 1999, pp. 1-7.

Chace, David, et al., "*Applications of a New Multiple Sensor Production Logging System for Horizontal and Highly-Deviated Multiphase Producers*," Society of Petroleum Engineers, Inc., SPE 63141, presented at 2000 SPE Annual Technical Conference and Exhibition, Dallas, TX, Oct. 1, 2000, pp. 1-14.

Hunt, James L., et al., "*Reservoir Characterization During Underbalanced Drilling: A New Model*," Society of Petroleum Engineers, Inc., SPE 59743, presented at 2000 SPE/CERI Gas Technology Symposium, Calgary,Alberta Canada, Apr. 3, 2000, pp. 1-10.

Kardolus, Christel, *Testing While Underbalanced Drilling*, Jul. 1997, Delft University of Technology, 94 pgs.

Cox, Richard J.W., *Testing Horizontal Wells While Drilling Underbalanced*, Delft University of Technology, Aug. 1998, 68 pgs.

Schoell, Martin, "Genetic Characterization of Natural Gases," *The American Association of Petroleum Geologists Bulletin*, V.67, No. 12, Dec. 1983, pp. 2225-2238.

Schoell, Martin, et al., "Gas Isotope Analyses While Drilling (GIA-WD): An Emerging Technology for Exploration, Production and Formation Evaluation," Poster Presentation under Theme 3 at the *AAPG National Convention*, Denver, 2001, pp. 1-27.

Ostroot, Kent, et al., "Reservoir Analysis During Underbalanced Drilling Yields Production, Reserves Increases," *Offshore*, Jun. 2004, pp. 2-3.

Minney, Blaine , et al., "New UBD Solutions Enable Real-Time Well Analysis," *The American Oil & Gas Reporter*, Sep. 1999, pp. 65-68.

Vefring, Erlend H., et al., "*Reservoir Characterization during UBD: Methodology and Active Tests*," Society of Petroleum Engineers, IADC/SPE 81634, presented at IADC/SPE Underbalanced Technology Conference and Exhibition, Houston, TX Mar. 25, 2003, pp. 1-9.

Biswas, D., et al., "*An Improved Model to Predict Reservoir Characteristics During Underbalanced Drilling*," Society of Petroleum Engineers, SPE 84176, presented at SPE Annual Technical Conference and Exhibition, Denver, CO, Oct. 5, 2003, pp. 1-11.

Vefring, Erlend H., et al., "*Reservoir Characterization during Underbalanced Drilling: Methodology, Accuracy, and Necessary Data*," Society of Petroleum Engineers, SPE 77530, presented at Annual Technical Conference and Exhibition, San Antonio, TX, Oct. 29, 2002, pp. 1-9.

Daigle, Chan, et al., "Optimizing the Reservoir Using an Underbalanced Environment," *Offshore*, Oct. 1998, 5 pgs.

Calibrated Instruments, Inc., materials from Website, 8 pages <http://www.calibrated.com>, visited Oct. 29, 2004.

Thermo Electron Corporation, materials from Website, copyright 2004, 8 pgs. <http://www.thermo.com>, visited Oct. 29, 2004.

Isotech Laboratories, materials from Website, Copyright 1997-2004, 41 pages <http://www.isotechlabs.com>, visited Oct. 29, 2004.

van Kruijsdijk, Cor P.J.W., et al., "*Testing While Underbalanced Drilling: Horizontal Well Permeability Profiles*," Society of Petroleum Engineers, SPE 54717, presented at 1999 SPE European Formatikon Damage Conference, The Hague, The Netherlands, May 31, 1999, pp. 1-9.

Hunt, James L., et al., "*Multilayer Reservoir Model Enables More Complete Reservoir Characterization During Underbalanced Drilling*," Society of Petroleum Engineers, IADC/SPE 81638, presented at IADC/SPE Underbalanced Technology Conference and Exhibition, Houston, TX, Mar. 25, 2003, 6 pages.

Kneissl, Wendy, "*Reservoir Characterization Whilst Underbalanced Drilling,*" Society of Petroleum Engineers, SPE/IADC 67690, presented at SPE/IADC Drilling Conference, Amsterdam, The Netherlands, Feb. 27, 2001, 9 pages.

Hunt, James L., "*Reservoir Data Integration,*" Halliburton, Presentation Apr. 1999, 20 pages.

Bourdarot, Gilles, Well Testing: Interpretation Methods (English translation), Institut Français Du Pétrole Publications, Copyright 1998, 318 pages.

McLennan, John, et al., Underbalanced Drilling Manual, Gas Research Institute, GRI-97/0236, Copyright 1997, 500 pages.

Cossé, René, Oil and Gas Field Development Techniques 13 Basics of Reservoir Engineering, Institut Français Du Pétrole, 1993, 369 pgs.

File History for U.S. Appl. No. 11/960,572, entitled "Characterizing a Reservoir in Connection With Drilling Operations" filed Dec. 19, 2007 (Total 139 pages on Jul. 30, 2009) and now U.S. Patent Application Publication No. 20080099241.

\* cited by examiner

SYSTEM FOR PREDICTING CHANGES IN A DRILLING EVENT DURING WELLBORE DRILLING PRIOR TO THE OCCURRENCE OF THE EVENT

CLAIM OF PRIORITY

This application is a divisional of and claims the benefit of priority under 35 U.S.C. §120 to prior U.S. patent application Ser. No. 10/844,725, filed May 12, 2004 now U.S. Pat. No. 7,337,660, which is incorporated herein by reference in its entirety.

TECHNICAL FIELD

This invention relates to characterization of oil and gas reservoirs, and more particularly to reservoir characterization in connection with drilling operations.

BACKGROUND

A reservoir is formed of one or more subsurface rock formations containing oil and/or gas. The reservoir rock is porous and permeable. The degree of porosity relates to the volume of liquid and gas contained in the reservoir. The permeability relates to the reservoir fluid's ability to move through the rock and be recovered for production to the surface.

Reservoirs are conventionally drilled overbalanced in which drilling fluid, chemicals and weighted material are circulated into and out of the well bore to maintain well control by making hydrostatic pressure in the well bore exceed the reservoir's pressure. A disadvantage in drilling overbalanced is formation damage that occurs when solids, fines and chemicals that are circulated into the well bore to maintain the overbalanced condition penetrate into the formation. Such penetration, or skin damage, impedes or stops hydrocarbons that would otherwise flow into the well during production operations.

Reservoirs may also be drilled at balance, near balance or under balanced. For under balanced drilling, drilling fluids with lower specific gravities are used such that hydrostatic pressure in the well bore is less than the reservoir's pressure. This allows hydrocarbons to flow into the wellbore when the formation is drilled. The hydrocarbon inflow reduces or prevents entry of drilling fluids and associated contaminants into the formation and thereby reduces formation skin damage. Higher production rates typically result from under balanced drilling.

During or after drilling, reservoirs are evaluated to determine the type, amount and value of contained hydrocarbons. The characteristics of a reservoir may be extrapolated from the small portion of a formation exposed during the drilling process. For example, data may be collected from drilling, well testing, logging and coring operations.

Reservoir evaluation may be aided by underbalance drilling in which reservoir fluids are allowed to flow into the well during drilling. Drilling fluid, gas and formation samples may be taken for laboratory analysis. Such analysis is typically performed after the completion of drilling operations. For example, the analysis may be performed during production logging or testing operations.

On site reservoir evaluation systems have also been used for under balanced drilling. Such systems provide mud logging and basic compositional analysis data. This data, along with pressure and rate data, has been used in connection with well bore modeling to determine reservoir permeability and other productivity information during drilling. Such information, however, is typically not available for wells drilled overbalanced or wells that oscillate between over and under balanced.

SUMMARY

Reservoir characterization in connection with drilling operations is performed based at least in part on reservoir fluid analysis during drilling. The drilling may be under balanced, near balanced, at balanced or over balanced.

In accordance with one embodiment, a method for reservoir characterization includes analyzing reservoir fluids by determining composition and isotopes of injection fluids injected into a wellbore during a drilling operation and production fluids recovered from the wellbore during the drilling operation. Reservoir fluids from a reservoir intersected by the wellbore are characterized based on the composition and isotopes of the injection fluid and of the production fluid.

Technical advantages of one or more embodiments include on-site reservoir geochemical characterization in connection with drilling operations. The reservoir geochemical characterization data may be integrated with productivity data to provide an improved reservoir characterization. In addition, the reservoir geochemical characterization may be performed in connection with under balanced, near balanced, at balanced or over balanced drilling operations. Accordingly, reservoir characterization may be provided in many or all drilling conditions.

Another technical advantage of one or more embodiments includes providing reservoir geochemical characterization and real-time or near real-time with a drilling operation. Accordingly, the reservoir including the reservoir fluids and reservoir productivity may be characterized during drilling and the information used to aid drilling decisions.

Still another technical advantage of one or more embodiments includes providing reservoir characterization in reservoirs that are amenable to under-balanced, near balanced, at balanced or over balanced drilling where the driver is either to minimize formation damage and/or obtain reservoir information for analysis. The fluid characterization may be used during the primary production phase, depleted and/or secondary recovery or tertiary recovery stage. Moreover, the fluid characterization can be used to determine the source of oil, gas and/or water, whether there is an up dip hydrocarbon, whether a shale is sealing or leaking, the source of production from a fracture, interconnectivity of a fracture system, water flood status, early breakthrough of a region, sweep efficiencies of water or gas floods, and/or bypassed oil. Fluid characterization may also aid in optimizing or otherwise enhancing completion methods, multi-well drilling campaigns and/or the drilling plan of an entire field.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
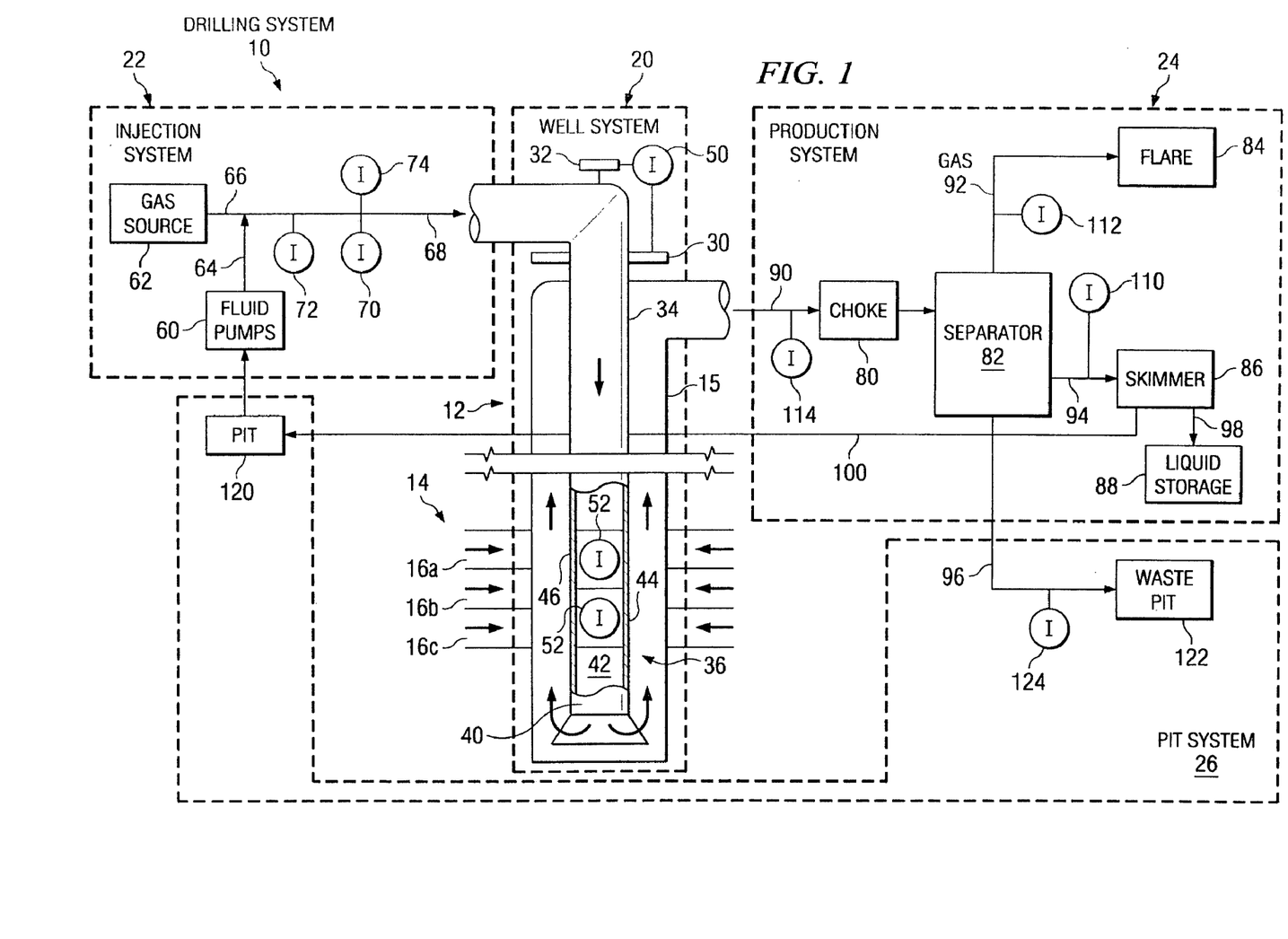
FIG. 1 illustrates one embodiment of a drilling system for an oil well.

FIG. 1 illustrates a drilling system 10 for an oil well 12. As used herein, oil well 12 includes any well intersecting a hydrocarbon reservoir 14. Oil well 12 includes well bore 15 and may intersect one or a plurality of reservoirs 14. As described in more detail below, reservoir 14 is porous and permeable rock containing liquid and/or gaseous hydrocarbon. The reservoir 14 may have a plurality of zones 16a, 16b, and 16c, each having disparate porosities, permeabilities, heights, fluids, and/or other characteristics. The reservoir 14 may be in a primary production phase, a depleted or secondary recovery phase or a tertiary recovery state.

Referring to FIG. 1, the drilling system 10 includes a well system 20, an injection system 22, a production system 24 and a pit system 26. The well system 20, injection system 22, production system 24 and pit system 26 may be part of a rotary or other suitable drilling rig. For example, the drilling system 10 may be a jack-up rig, semi-submersible rig, mobile offshore drilling unit (MODU), land based drilling rig, or other unit operable to bore through the earth to resource-bearing or other geologic formations.

The well system 20 includes the well 12, and surface equipment including a rotary table 30 and lifting gear 32. The well system 20 also includes a drill string 34 and a bottom hole assembly (BHA) 36. Rotary table 30 rotates a drill string 34 and thus the BHA 36 during conventional drilling operations. A top-drive or other suitable unit may be used in place of the rotary table 30.

The lifting gear 32 may in one embodiment include a crown block mounted to a mast and a traveling block interconnected to the crown block by a cable that is driven by draw works to control upward and downward movement of the traveling block. The traveling block may carry a hook from which is suspended a swivel that supports a kelly, which in turn supports the drill string 34. The well system 20 may include other surface equipment such as blowout preventers (BOPs) positioned at the top of the well 12 and slips to hold the drill string 34 during connections.

The drill string 34 may comprise a plurality of interconnected sections of drill pipe, coiled tubing, or other suitable piping. The BHA 36 in one embodiment includes a rotary drilling bit 40, a downhole motor 42, a measurement while drilling (MWD) device 44 and a pressure while drilling device (PWD) 46. The drilling bit 40 may be a conventional tri-cone or other suitable bit. The downhole motor 42 may be a conventional bent sub with a fluid motor for directional drilling. The MWD 44 and PWD 46 may be conventional devices operable to collect and/or report downhole geometries, pressures and/or other measurements.

The well system 20 may include both surface and downhole instrumentation to collect and/or report data on the drilling operation. In one embodiment, surface data logging (SDL) instruments 50 may be provided at the surface on the rig. The SDL instruments 50 measure, record and/or report data from the rotary table 30, the lifting gear 32 and other surface equipment. For example, SDL instrumentation 50 may record data on rotary table torque, measured and total vertical depth of the well 12, hook load, rate of penetration (ROP), weight on bit (WOB), revolutions per minute (RPM), bit hours, bit revolutions, drilling fluid type and the like.

The MWD 44 and PWD 46 may include downhole instruments 52. The downhole instruments 52 measure, record and/or report downhole pressure and temperature data as well as geometric data such as inclination and azimuth of the BHA 36. Downhole instruments 52 may also include gamma, resistivity and other downhole measuring devices.

Data gathered by downhole instruments 52 may be communicated to the surface during drilling operations by electric wire line, fluid pressure pulse, acoustic or other suitable processes and/or may be recorded for later use. In a particular embodiment, all data received by MWD 44 and PWD 46 is recorded for later collection and use while a subset of the data is communicated to the surface during drilling operations. As used herein, during drilling operations means operations between spudding of the well 12 and removal of the bit 40 once total depth (TD) of the well 12 has been reached. For example, drilling activity may include the use of multiple drill bits 40 and tripping of the drill string 34 one or more times to change the drill bit 40. Thus, a drilling operation may include intermediate testing, circulation, calibration and other operations and construction of the wellbore 15 need not be continuous.

The injection system 22 includes fluid pumps 60 and gas source 62. The fluid pumps 60 pump drilling fluid 64 from the pit system 26 into the drill string 34. Gas source 62 may be a compressor or other source of compressed gas for under balanced, near balanced and/or at balanced drilling of the well 12. In some embodiments, the well 12 may be drilled in multiple conditions, may oscillate between conditions, and may be drilled substantially or fully in one condition. The well 12 may also be drilled partly or fully over balanced. Drilling gas 66 from source 62 is mixed with the drilling fluid 64 to form drilling fluid 68 that is injected into the drill string 34 or the stand pipe or other line coupled to the drill string 34.

Although not shown, a tracer material may be added to drilling fluid 68 to aid in measuring elapsed time from injection of the drilling fluid 68 to return at the surface in the production system 24. Elapsed time from the injection of the tracer until reappearance of the tracer indicates the circulation time. The tracer material may be a carbide, an inert substance such as a neon gas, a gas or liquid not usually found naturally occurring in commercially drilled hydrocarbon bearing reservoirs, or a short half-life radioactive material or other suitable material.

The injection system 22 includes instruments for measuring, recording and/or reporting data for the upstream drilling fluids. In a particular embodiment, a liquid analyzer instrument 70 may be coupled to the stand pipe or other drilling fluid injection line to analyze the composition of the injected drilling fluid 68. In this embodiment, the liquid analyzer instrument 70 may provide full compositional analysis of liquids in the injected drilling fluid 68. The full compositional analysis identifies all, substantially all or significant hydrocarbons and other liquids present in trace amounts or other suitable amounts, including water, chlorides and other chemicals. The Liquid, gas or other fluid is significant when its detection materially contributes to characterization of reservoir fluids and/or the reservoir 14. In a particular embodiment, a chromatograph may be used to provide the full compositional analysis on site in real-time or near real-time. As used herein, near real-time means during the drilling operation. In another embodiment, compositional analysis of the injected drilling fluid 68 may be performed off site and/or after the completion of the drilling operation.

A gas analyzer instrument 72 may also be coupled to the stand pipe or other injection line to analyze the injected drilling fluid 68. In a particular embodiment, the gas analyzer instrument 72 includes a composition analyzer and an isotope analyzer that together measure composition and isotopes of hydrocarbons, non-hydrocarbons and trace gases. The isotope measurement "fingerprints" gases in the drilling fluid 68. In a particular embodiment, the gas analyzer instrument 72 may comprise a gas chromatograph that measures C1-C5 and possibly higher molecular weight hydrocarbons as well as nitrogen, oxygen, argon and measurable trace gases. In another embodiment, the gas analyzer instrument 72 may comprise a mass spectrometer, laser spectrometer other instrument operable to provide a full compositional analysis of gases as well as identify isotopes present in significant hydrocarbon, non-hydrocarbon and trace gases. In another embodiment, the gas analyzer instrument 72 may comprise a laser spectrometer operable to detect carbon-13 and deuterium. The liquid and/or gas analyzer instruments 70 and 72 may measure any tracer added to the drilling fluid 68.

The injection system 22 may also include injection parameter instruments 74 coupled to the stand pipe 34 or other injection line. Injection parameter instruments 74 may in one embodiment measure pressure, temperature and/or flow rate of the drilling fluid 68 injected into the drill string 34. The injection parameter instruments 74 may also in some embodiments measure resistivity, volume, density and/or other characteristics of the drilling fluid 68.

The production system 24 includes a choke 80, separator 82, gas flare 84, skimmer 86 and liquid storage 88. The choke 80 regulates pressure of production fluid 90 returning from the annulus of well 12. The separator 82 may be a single or multiple stage separator that separates gases, liquids and solids. In a particular embodiment, the separator 82 may separate gas 92, liquids 94 and solid cuttings 96. The gas 92 may be flared by gas flare 84. Liquids 94 may be processed by skimmer 86 which separates oil 98 from drilling fluid and water 100. The oil 98 may be stored in liquid storage 88. The drilling and water fluid 100 may be deposited in the pit system 26 for processing and/or recirculation into the well 12 in connection with drilling operations.

The production system 24 includes instruments for measuring, recording and/or recording data for the downstream drilling fluids. In a particular embodiment, a liquid analyzer instrument 110 is coupled to a liquid output of the separator 82 and a gas analyzer instrument 112 is coupled to the gas outlet of the separator 82. The liquid analyzer instrument 110 provides a full compositional analysis of the liquid effluent from the separator 82. In one embodiment, the liquid analyzer instrument 110 may be the same or similar as liquid analyzer instrument 70 of the injection system 22.

The gas analyzer instrument 112 may include a gas composition analyzer and an isotope analyzer. The gas composition analyzer provides a full compositional analysis of the production gas 92, including hydrocarbon, non-hydrocarbon and trace gases. The isotope analyzer determines the isotopes present in the production gas 92. The gas analyzer instrument 112 may be the same or similar as the gas analyzer instrument 72 of the injection system 22.

The production system 24 may also include production parameter instruments 114 coupled to the well return line. The production parameter instruments 114 may measure pressure, temperature and/or flow rate of production fluid 90. The production parameter instruments 114 may also in some embodiments measure resistivity, volume, density and/or other characteristics of the production fluid 90. The production parameter instruments 114 may be the same or similar as the injection parameter instruments 74 of injection system 22.

The pit system 26 includes pit 120 and waste pit 122. Pit 120 receives, stores and processes drilling fluid and water 100 for recirculation into the well 12 during drilling operations. The pit 120 may include shakers, desanders, degasers, desilters and hoppers, as well as intermediate, active and trip tank pits. Flow rate, volume and/or level sensors in the pit 120 may form part of SDL instruments 50.

Solid formation cuttings 96 separated by separator 82 from the production fluid 90 are disposed of in the waste pit 122. A cuttings analyzer instrument 124 may be coupled to the waste line and either manually controlled or automatically controlled to sample cuttings 96. Cuttings analyzer instrument 124 may rapidly evolve fluids out of the cuttings 96 for on site and/or near real-time analysis. In one embodiment, the cuttings analyzer instrument 124 mechanically crushes, agitates and/or heats the cuttings 96 to evolve fluids within minutes, an hour, a couple hours, part of a day or a day or more. In another embodiment, cuttings 96 may be otherwise vibrated by ultrasonic energy or otherwise to reduce surface tension and free the contained fluid. The cuttings analyzer instrument 124 may include a liquid analyzer and a gas analyzer to determine the composition of liquid and the composition and isotopes of gas evolved from the cuttings 96. The gas analyzer may include a constant flow system such that nitrogen or other gas remains flowing in the absence of gas from the cuttings. In another embodiment, the cuttings 96 may be mechanically sampled. The cuttings may also be partly or fully analyzed off site.

During drilling operations, drilling is accomplished by applying weight to the bit 40 and rotating the drill string 34, which in turn rotates the bit 40. The drill string 34 is rotated within the well bore 15 by action of the rotary table 30. Alternatively or in addition, the downhole motor 42 may rotate the bit 40 independently of the drill string 34 and rotary table 30 for directional drilling. Cuttings 96 are produced as the bit 40 drills into the earth and are carried out of the wellbore 15 by circulating the injected drilling fluid 68 supplied by fluid pumps 60 and/or additionally carried by produced reservoir fluids.

Data collected by instruments of the well system 20, injection system 22, production system 24 and pit system 26 may be provided to a reservoir characterization system 200 (shown in FIG. 3) for processing and analysis. The instruments may be connected to the reservoir characterization system 200 by electrical wire line or wireless links. For example, the instruments may be directly hard wired to the reservoir characterization system 200 or may be connected to the reservoir characterization system 200 by a local area network (LAN) such as an Ethernet. In another embodiment, some or all the instruments may communicate with the reservoir characterization system 200 by radio frequency (RF) or other suitable links.

Figure 2:
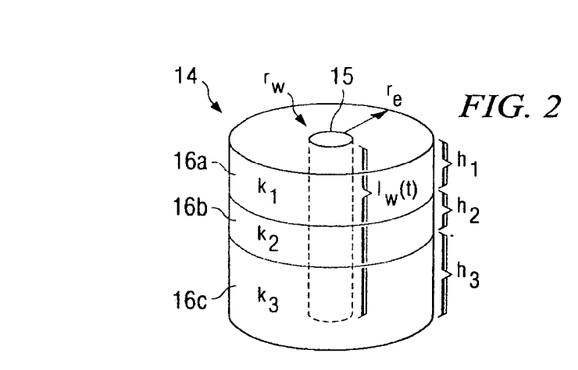
FIG. 2 illustrates one embodiment of the reservoir of FIG. 1.

FIG. 2 illustrates details of one embodiment of the reservoir 14. As previously described, the reservoir 14 may include multiple zones 16A, 16B and 16C. Each zone 16, or layer, may have its own thickness h and permeability k, as well as other reservoir properties.

Referring to FIG. 2, the reservoir 14 has an outer boundary at $r=r_e$. The wellbore 15 has a radius $r_w$ and is drilled at the center of the reservoir 14. At time $t=0$ the total well rate q and the total length of the well $l_w$ are 0. During drilling at a later time t, the well has a rate of $q(t)$ and a length $l_w(t)$. As the well bore 15 traverses each zone 16, the flow across the sandface instantaneously redistributes. A method of modeling the flow into the wellbore may be to assume the flux into the well bore 15 is uniform over each zone 16. However, there may be a different flux in each zone 16.

Figure 3:
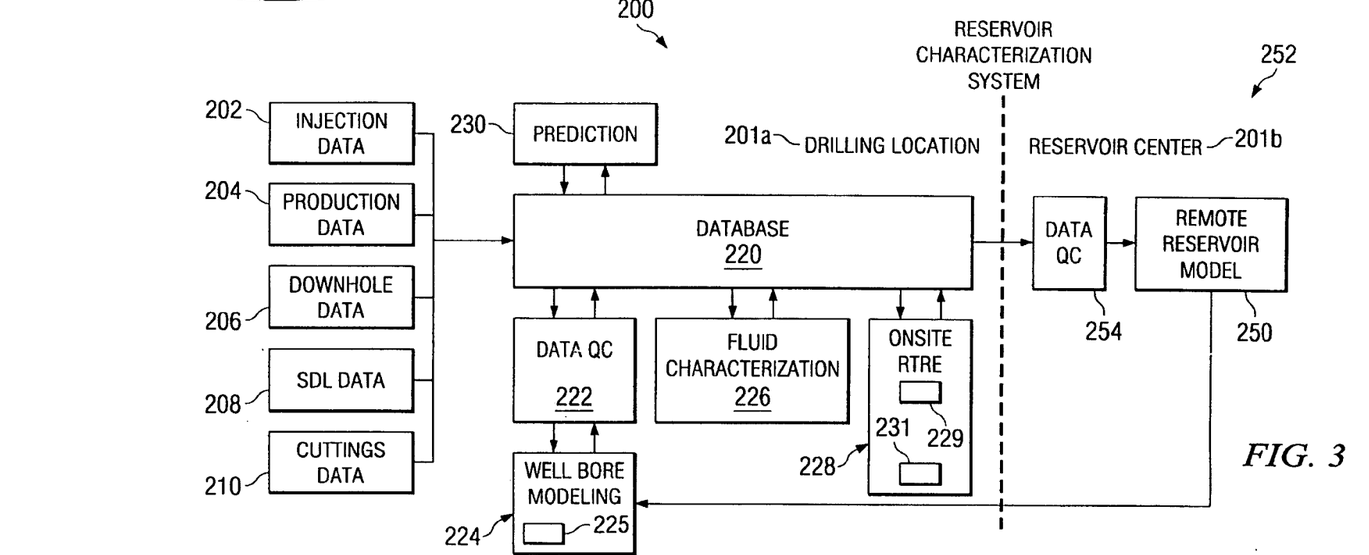
FIG. 3 illustrates one embodiment of a reservoir evaluation system for use in connection with the drilling system of FIG. 1.

FIG. 3 illustrates the reservoir characterization system 200 in accordance with one embodiment. In this embodiment, the reservoir characterization system 200 is a distributed system including on-site processing at the drilling location 201*a* and remote processing at a reservoir center 201*b*. The elements of the reservoir evaluation system 200 may be otherwise suitable distributed and/or combined. The on-site and remote components may communicate via wire line and/or wireless links. For example, communication may be provided over a satellite link. Reservoir characterization may comprise reservoir evaluation and/or additional evaluation and characterization.

Referring to FIG. 3, reservoir evaluation system 200 includes at the drilling location 201*a* a data collection system comprising injection data 202, production data 204, downhole data 206, SDL data 208 and cuttings data 210. The injection data 202 is collected from instruments 70, 72 and 74 of the injection system 24. In particular, the injection data 202 may include the pressure, temperature and flow rate of drilling fluid 68 injected into the drill string 34 as well as the composition and isotopes of the liquid and gas in the drilling fluid 68. The injection data 202 may have various sampling rates. For example, the pressure, temperature and flow rate data may be sampled one or more times every second or every several seconds while the composition and isotopes may be sampled once a minute or every several minutes. Other suitable sampling rates may be used for the injection data 202.

The production data 204 includes data collected from instruments 110, 112 and 114 of the production system 24. In particular, the production data 204 may include the pressure, temperature and flow rate of production fluid 90 recovered from the annulus of the wellbore 15. The production data 204 may also include the composition and isotopes of the liquid and gas in the production fluid 90. Production data 204 may be sampled at the same or similar rates as injection data 202.

The downhole data 206 may comprise data collected from instruments 52 of MWD 44 and PWD 46. In particular, the downhole data 206 may include geometric data as well as downhole temperature and pressure. The downhole data 206 may also include resistivity and gamma data. As previously described, the downhole data 206 may be communicated to the surface via fluid pressure pulse or otherwise. Downhole data 206 may be sample every few seconds, every few minutes or otherwise suitably.

The SDL data 208 may comprise data collected from instrument 50 of well system 20 as well as other surface instruments. In particular, SDL data 208 may include hook loads, depths, rotary torque, ROP, WOB, RPM, bit hours, bit revolutions, drilling fluid type, tank temperatures, pressures and levels, fluid pH and other parameters of the drilling operation. The SDL data 208 may be sampled at any suitable rates including several times a second, every one or more seconds, several times a minute, every one or more minutes, several times an hour or every one or more hours. As with the other data, the SDL data 208 may be sampled automatically and/or manually.

The cuttings data 210 includes data collected by instrument 124. In particular, cuttings data 210 may include the composition and isotopes of fluid recovered from cuttings 96. The cuttings 96 may be manually or automatically sampled. The sampling rate may be every several minutes, every several hours, or otherwise suitably.

The injection data 202, production data 204, downhole data 206, SDL data 208 and cuttings data 210 is communicated to a database 220. Each item of data may be associated with a time stamp for cross-correlation by the reservoir characterization system 200. The time stamp may indicate the time when the data was initially recorded and/or the time the data was received by database 220. Also recorded in the database 220 may be the depth of the drilled wellbore 15 corresponding to when the item of data was obtained. The database 220 may be a relational or any other suitable database.

The database 220 may be coupled to a quality control (QC) or data cleansing unit 222, modeling unit 224, fluid characterization unit 226, on site real-time reservoir evaluation (RTRE) unit 228 and prediction unit 230. Each unit 222, 224, 226, 228 and 230 may comprise a neural network, artificial intelligence and/or other suitable processors.

Data cleansing unit 220 may validate measured data and compensate for any missing data. Validation may include filtering out spurious signals based on instrument and/or operating limits. Data cleansing unit 220 may compensate for missing data by filling in the data using pattern matching, running averages and other suitable techniques. The cleansed data may be provided back to the database 220 for storage and to modeling unit 224.

Modeling unit 224 includes a well bore model 225. The well bore model 225 may be a steady state or a transient model. In addition, the well bore model 225 may be a forward mode model or a reverse mode model. In the forward mode model, injection rates and pressures and reservoir influx rates are measured and production rates are calculated based on measured data. For the forward mode model, the reservoir influx rates may be measured by a downhole flow measurement instrument such as that described in U.S. Pat. No. 6,585,044 which is hereby incorporated by reference.

In the reverse mode model, injection and production rates and pressures are measured and reservoir influx rates back calculated based on measured rates and pressures. For back calculation, surface injection data is lag shifted forward to downhole conditions while production data is lag shifted backwards to downhole conditions. The lag shift is the time difference between presence at the surface and downhole and is used to correlate surface conditions to downhole conditions. Gases, liquids and solids may have disparate lag shifts.

After injection and production data is lag shifted to downhole conditions, the wellbore model 225 performs a material balance to determine reservoir response, or net influx of fluids versus time during the drilling operation. In one embodiment, separate gas and liquid material balances are performed. In this embodiment, the material balance for gases may be determined by multiplying the total injection rate of gas by the injection compositional analysis for each gas component compared against the total production rate of gas multiplied by the production compositional analysis for each gas component. The material balance for liquids may be determined by multiplying the total injection rate of liquid by the injection compositional analysis for each liquid component compared against the total production rate of liquid multiplied by the production compositional analysis for each liquid component. In determining the material balances for gases and liquids, compensation may be made for phase changes due to the nature of reservoir fluids and pressure and temperature changes. In one embodiment, compensation may be preformed with the lag calculations. The material balance and phase changes may be otherwise suitably performed. In addition, the material balance may be partly or fully performed by the RTRE unit 228.

Lag of cuttings 96 may in one embodiment be determined using tracers that are added to the fluid, or mud, and adhere to the cuttings 96. In a particular embodiment two or more fluorescent dyes are added to the fluid stream 68. As the drill bit 40 grinds cuttings 96, some of the fluorescent dye is ground into the cuttings 96. The efficiency with which the dye is bound to the cuttings 96 may differ from rock type to rock type, however, if the character of the fluorescent dyes are similar, then the ratio of concentrations of fluorescent dyes will stamp when those cuttings 96 were ground within the spread of the fluorescent dye plug down hole. In this embodiment the concentration of tracer is known and may be injected continuously or discretely. The lag of fluid in the down hole trip is also known. With the ratio of tracer signals or similar mathematical operation which may comprise more than two tracers, the returned cuttings tracer profile can be related to the inserted tracer profile and time-depth stamped with the lag information. In another embodiment, a property proportional to the concentration of fluorescent dye may be used. The fluorescent signal alone may be suitable. In this embodiment, a fluorescence meter could suffice. Other tracer types and analytical equipment could suffice in alternative embodiments.

In other embodiments of reverse mode model, disparate data may be used to determine the net influx of fluids versus time. For example, geothermal gradients may be used to determine downhole temperature. Pressure may only be measured at the surface extrapolated to downhole conditions or may only be measured downhole.

To aid wellbore modeling, drilling of the wellbore 15 may be calibrated during drilling with the wellbore models. Calibration, in one embodiment, may allow changes in measurements that result from reservoir response of each zone 16 to be detected. In a particular embodiment, calibration is performed by stopping drilling for flow test and for pressure testing while shut-in or circulating. Data obtained from the flow and pressure test are compared with the wellbore model. If the model does not match observed conditions, the model may be tuned, updated by the reservoir center 201B or otherwise adjusted. Calibration may be performed above and/or within each zone 16. To enhance or maximize information obtained from the drilling process, a zone 16 may in one embodiment be drilled entirely under balanced at a controlled rate with incremental production and pressures monitored using the instrumentation described above.

Fluid characterization unit 226 provides geochemical analysis of and characterizes produced effluent from the well 12. The fluid characterization may be performed regardless of whether the well 12 is drilled under balanced, near balance, at balance, over balanced or oscillating between two or more conditions. In particular, fluid characterization unit 226 may analyze reservoir fluids in each productive zone 16 as the zone is traversed and may make the composition and isotopes of produced effluents available during drilling and/or after drilling to reservoir engineers and geoscientists. Fluid characterization unit 226 may also determine and plot ratios and trends of compositions versus time. The fluid characterization unit 226 may be used to determine the source of oil, gas and/or water, whether there is up dip hydrocarbon that was missed, whether a formation is sealing or leaky, the source of production from a fracture, interconnectivity of a fracture system, water flood status, early breakthrough in a region, sweep efficiencies of water or gas floods, bypass oil and aid in optimizing completion methods and multi-well drilling campaigns.

The compositional and isotope analysis may also aid in distinguishing zones 16 in the well 12, in correlating the zones 16 of the well 12 with those of other wells, and understanding the origin of the reservoir fluids. The compositional and isotope information developed by the fluid characterization unit 226 may be stored back in the database 220 and used by RTRE unit 228 in evaluating the reservoir 14. For example, analysis by the fluid characterization unit 226 may provide information on the circulating fluids and changing phases of the fluid for the RTRE unit 228. The fluid characterization unit 226 may also aid in defining the completion mechanism for the well 12 and in correlating cuttings 96 with specific zones 16 of the reservoir 14. The fluid characterization unit 226 may additionally provide profiles of reservoir fluids from each zone 16.

The on site RTRE unit 228 includes a reservoir model 229 that provides an on site evaluation of the reservoir 14. The reservoir model 229 in one embodiment utilizes sandface rates and pressures calculated by the wellbore model and historical data from similar wells determine the heights, and permeabilities k of the zones 16 of the reservoir 14. In a particular embodiment, the reservoir model 229 is a multi-layered model constructed from a single-layer model with the use of superposition and the assumption of crossflow only in the wellbore 15. The single-layer model may be a transient well test model with the exception that the length of the completion interval changes with time in the drilling process, which may be accounted for by assuming flow across the sandface instantaneously redistributes as the well 12 is drilled so that the flux across the sandface is always uniform. The flux is selected in each layer 16 to proximate a constant pressure inner boundary. The pressure of the wellbore 15 ties the layers 16 together through the pressure drop from zone to zone. In operation, the pressure is measured at the BHA 36 and the pressure is back-calculated across each zone 16 already drilled. Because the permeabilities of the already drilled layers 16 have been calculated, the influx rates from the already drilled zones 16 may be determined. The rates from these already drilled zones 16 may then be subtracted from the total measured influx rate to determine the rate of a newly opened zone 16. The permeability of the new zone may be varied in a trial and error fashion to match the calculated rate. This permeability for the newly opened layer may then be used in the calculations for the next zone 16. Historical data for the reservoir model 29 may be provided and/or updated from the reservoir center 201B. Other suitable reservoir models 229 operable to determine permeability of the zones 16 in the reservoir 14 may be used.

Based on permeability, the on site RTRE unit 228 may generate a productivity index (PI) for each zone 16 and may also generate in flow production rate (IPR) curves, extrapolate the IPR curves to determine virgin reservoir pressure P* of the reservoir 14 or for a specific zone 16 of the reservoir 14. Fracture transmissibility Kh and skin effect S may also be determined by the on site RTRE unit 228 based on measured data and the reservoir model 229. In a particular embodiment, the reservoir model 229 may in addition to accounting for variances attributable to multiple formation layers, may account for partial penetration of a zone, dual porosity of the reservoir 14 and occurrence of vertical, horizontal or high angle wellbores as well as other variations and parameters. Data from the on site RTRE unit 228 may be employed by reservoir engineers, geologists and others to more accurately project well production and reservoir estimates from the reservoir 14.

In one embodiment, the on site RTRE unit 228 includes a deconvolution application 231 which utilizes the composition and isotope information from fluid characterization to "fingerprint", or identify the produced effluent from each zone 16 of the reservoir 14 and thereby provide improved correlation of productivity for the zones 16. In particular, the proportion in the produced effluent from each zone 16 may be linked to the flow rate for each zone by measuring the mix composition and using the composition from each zone to determine the flow rate from each zone. This integration of fluid characterization information with the productivity information from reservoir evaluation provides, in one embodiment, a more complete reservoir characterization. The reservoir characterization may be provided in real time or near real-time. During drilling operations or otherwise in connection with drilling operations, reservoir characterization and/or data is provided in connection with drilling operations when the data or characterization is during drilling operations or based on data collected from drilling operations.

The prediction unit 230 monitors surface and downhole data and well inflows to predict drilling events. The prediction unit 230 may activate alarms for predefined drilling conditions. For example, a kick alarm may provide an early warning of a dangerous influx of formation fluids into the wellbore 15.

Reservoir center 201b includes remote reservoir model 250 and data QC or manipulator 252. The data manipulator 252 receives data from the database 220 and further cleanses the data using historical databases, running averages and the like. In a particular embodiment, the data manipulator 252 may comprise an averaging routine to enhance or optimize the number of data points available for the remote reservoir model 250. The remote reservoir model 250 may provide further analysis of the reservoir 14 and zones 16 based on testing and production information in connection with the drilling information. In one embodiment, the remote reservoir model 250 may perform a final interpretation and generate forecast of productions and economics for the well 12. The remote reservoir model 250 may also provide detailed reports, plots and data files for the well owner. In addition, providing data to the reservoir center 201B may allow for off site operation supervision and reservoir analysis by multi-disciplinary engineering and geology teams.

The remote reservoir model 250 may comprise a dual porosity model, a damage model, automated fluids property calculations including pseudo-pressures, an inclined well model and models for additional geometries, a discrete fracture model, bottom hole pressure and weight synchronization software, optimized history matching and a skin damage model versus time. These and/or other models may also be implemented partially or fully in the on site RTRE unit 228. Data from the remote reservoir model 250 may be fed back during drilling to the modeling 224 or to other units of the reservoir characterization system 200.

Figure 4:
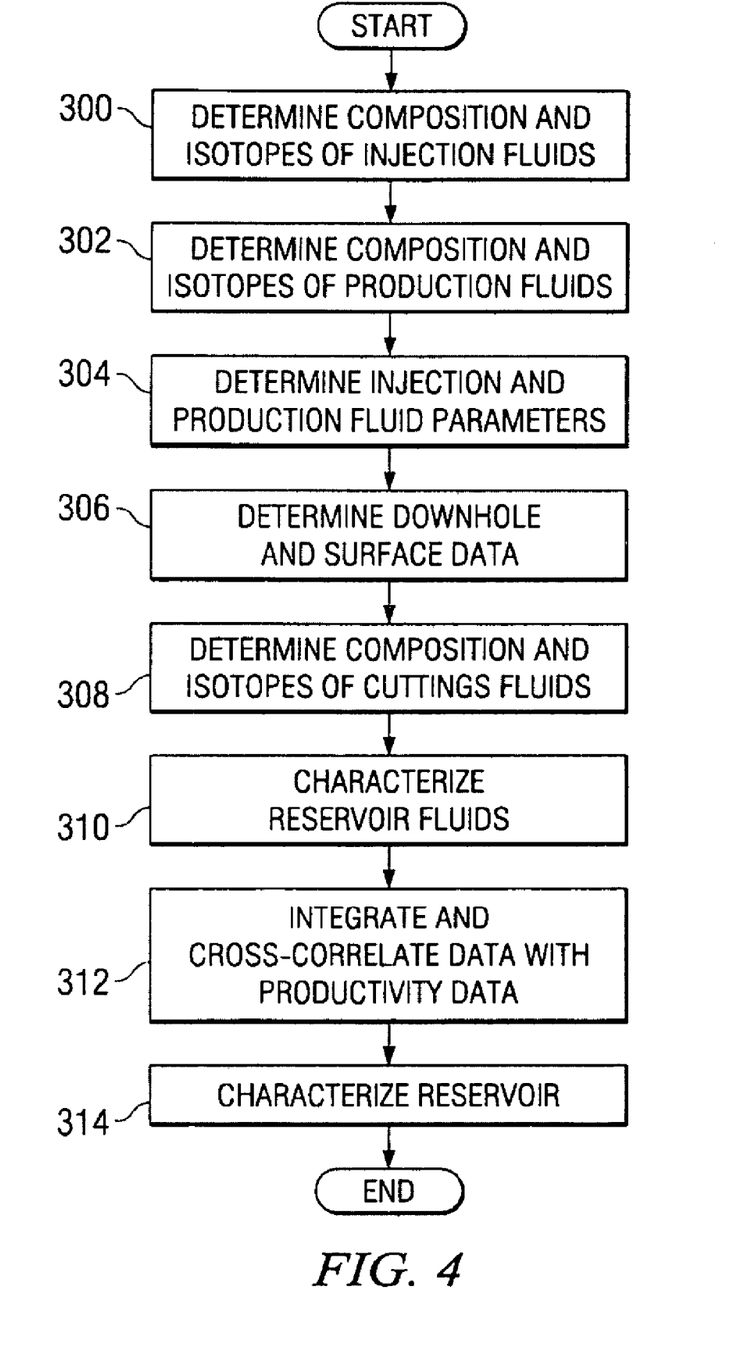
FIG. 4 illustrates one embodiment of a method for reservoir characterization based at least in part on reservoir fluid characterization.

FIG. 4 illustrates a method for reservoir characterization in accordance with one embodiment. The method begins at step 300 in which the composition and isotopes of upstream or injection drilling fluid 68 are determined. As previously described the composition and isotopes may be determined using the gas and liquid analyzers 70 and 72. Next, at step 302, the composition and isotopes of downstream or production drilling fluids 90 are determined. The composition isotopes may be determined using the gas and liquid analyzers 110 and 112. The composition data may comprise full compositional analysis data for hydrocarbon, non-hydrocarbon and trace fluids.

At step 304, injection and production fluid parameters are determined. In one embodiment, the upstream and downstream fluid parameters may comprise pressure, temperature and flow rate and may be determined using instruments 74 and 114. Next, at step 306, downhole and surface data for the drilling process are determined. The downhole data may be determined by MWD 44 and PWD 46. The surface data may be determined from rig instruments 50. At step 308, the composition and isotopes of fluids in the cuttings 96 are determined. In one embodiment, the cuttings 96 are agitated and heated by instrument 124 to evolve fluids for analysis in real time or near real-time.

At step 310, reservoir fluids are characterized based on the compositional and isotope data. Fluid characterization may be provided in real-time, near real-time or otherwise. At step 312, the fluids information is integrated and cross correlated with productivity data to provide at step 314 reservoir evaluation and characterization. Step 314 leads to the end of the process. If reservoir characterization is provided in real-time or near real-time, the characterization information may be used for drilling decisions. Reservoir characterization, even if provided after the completion of drilling, may provide for early project evaluation, and accelerated completion design. For example, reservoir characterization may be used to steer the direction of drilling to encounter bypass zones or sweet spots. The information could be used to determine whether it is necessary to drill deeper if production is already obtained from deeper zones due to good connectivity already established in the current zone. The information may also help determine the interconnectiveness across the field and the optimized completion strategy. It may also be used to optimize secondary injection/production strategy in a water flooding phase or tertiary recovery stage.

A number of embodiments of the invention have been described. Nevertheless, it will be understood that various modifications may be made without departing from the spirit and scope of the invention. Accordingly, other embodiments are within the scope of the following claims.

What is claimed is:

1. A system for drilling a wellbore, the system comprising: a prediction unit; and
the prediction unit operable to predict a change in a drilling event while the wellbore is being drilled into a reservoir and is underbalanced relative to the reservoir and prior to the drilling event change occurring.

2. The system of claim 1, wherein the prediction unit is included in a reservoir characterization system which receives data from instruments while the wellbore is being drilled.

3. The system of claim 1, wherein the data includes at least one of injection data, production data, downhole data, surface data, or cuttings data.

4. The system of claim 1, wherein the prediction unit includes at least one of a neural network and artificial intelligence.

5. The system of claim 1, wherein the drilling event change is a change in flow between the wellbore and a reservoir while the wellbore is being drilled and prior to the change in flow occurring.

6. The system of claim 1, wherein the prediction unit activates an alarm which warns of an increased influx of formation fluids into the wellbore.

7. The system of claim 1, wherein the prediction unit receives data from at least one of a reservoir model and a wellbore model.

8. A system for drilling a wellbore, the system comprising: a prediction unit; and
the prediction unit operable to predict a change in a drilling event while the wellbore is being drilled into a reservoir and is overbalanced relative to the reservoir and prior to the drilling event change occurring.

9. The system of claim 8, wherein the prediction unit is included in a reservoir characterization system which receives data from instruments while the wellbore is being drilled.

10. The system of claim 8, wherein the data includes at least one of injection data, production data, downhole data, surface data, or cuttings data.

11. The system of claim 8, wherein the prediction unit includes at least one of a neural network and artificial intelligence.

12. The system of claim 8, wherein the drilling event change is a change in flow between the wellbore and a reservoir while the wellbore is being drilled and prior to the change in flow occurring.

13. The system of claim 8, wherein the prediction unit activates an alarm which warns of an increased influx of formation fluids into the wellbore.

14. The system of claim 8, wherein the prediction unit receives data from at least one of a reservoir model and a wellbore model.

15. A system for drilling a wellbore, the system comprising:
   a prediction unit; and
   the prediction unit operable to predict a change in a drilling event while the wellbore is being drilled into a reservoir and is near balanced relative to the reservoir and prior to the drilling event change occurring.

16. The system of claim 15, wherein the prediction unit is included in a reservoir characterization system which receives data from instruments while the wellbore is being drilled.

17. The system of claim 15, wherein the data includes at least one of injection data, production data, downhole data, surface data, or cuttings data.

18. The system of claim 15, wherein the prediction unit includes at least one of a neural network and artificial intelligence.

19. The system of claim 15, wherein the drilling event change is a change in flow between the wellbore and a reservoir while the wellbore is being drilled and prior to the change in flow occurring.

20. The system of claim 15, wherein the prediction unit activates an alarm which warns of an increased influx of formation fluids into the wellbore.

21. The system of claim 15, wherein the prediction unit receives data from at least one of a reservoir model and a wellbore model.

22. A system for drilling a wellbore, the system comprising:
   a prediction unit; and
   the prediction unit operable to predict a change in a drilling event while the wellbore is being drilled into a reservoir and is balanced relative to the reservoir and prior to the drilling event change occurring.

23. The system of claim 22, wherein the prediction unit is included in a reservoir characterization system which receives data from instruments while the wellbore is being drilled.

24. The system of claim 22, wherein the data includes at least one of injection data, production data, downhole data, surface data, or cuttings data.

25. The system of claim 22, wherein the prediction unit includes at least one of a neural network and artificial intelligence.

26. The system of claim 22, wherein the drilling event change is a change in flow between the wellbore and a reservoir while the wellbore is being drilled and prior to the change in flow occurring.

27. The system of claim 22, wherein the prediction unit activates an alarm which warns of an increased influx of formation fluids into the wellbore.

28. The system of claim 22, wherein the prediction unit receives data from at least one of a reservoir model and a wellbore model.

29. A system for drilling a wellbore, the system comprising:
   a prediction unit including a neural network; and
   the prediction unit operable to predict a change in a drilling event while the wellbore is being drilled and prior to the drilling event change occurring.

30. The system of claim 29, wherein the prediction unit is included in a reservoir characterization system which receives data from instruments while the wellbore is being drilled.

31. The system of claim 29, wherein the data includes at least one of injection data, production data, downhole data, surface data, or cuttings data.

32. The system of claim 29, wherein the drilling event change is a change in flow between the wellbore and a reservoir while the wellbore is being drilled and prior to the change in flow occurring.

33. The system of claim 29, wherein the prediction unit receives data from at least one of a reservoir model and a wellbore model.

* * * * *